United States Patent [19]
Gilchrest et al.

[11] Patent Number: 5,962,417
[45] Date of Patent: Oct. 5, 1999

[54] METHODS OF MODULATING MELANIN SYNTHESIS

[75] Inventors: Barbara A. Gilchrest, Boston; Hee-Young Park, Chelsea, both of Mass.

[73] Assignee: Trustees of Boston University, Boston, Mass.

[21] Appl. No.: 09/160,126

[22] Filed: Sep. 24, 1998

Related U.S. Application Data

[63] Continuation of application No. PCT/US97/04752, Mar. 27, 1997, which is a continuation-in-part of application No. 08/623,364, Mar. 28, 1996, abandoned.

[51] Int. Cl.$^6$ .............................. A61K 38/00; C12N 9/16
[52] U.S. Cl. ................................ 514/12; 514/13; 514/14; 514/15; 514/16; 514/17; 435/196
[58] Field of Search ................................. 514/12, 13, 14, 514/15, 16, 17; 435/196

[56] References Cited

U.S. PATENT DOCUMENTS

| | | | |
|---|---|---|---|
| 4,621,023 | 11/1986 | Rezdiniak et al. | 428/402.2 |
| 4,880,635 | 11/1989 | Janoff et al. | 424/450 |
| 5,077,211 | 12/1991 | Yarosh | 435/193 |
| 5,147,652 | 9/1992 | Egyud | 424/450 |
| 5,219,748 | 6/1993 | Yoshitaka et al. | 435/194 |
| 5,324,651 | 6/1994 | Ono et al. | 435/194 |

FOREIGN PATENT DOCUMENTS

| | | |
|---|---|---|
| 0 584 452 A1 | 3/1994 | European Pat. Off. . |
| 0 679 660 A1 | 11/1995 | European Pat. Off. . |
| 92/18149 | 10/1992 | WIPO . |
| 95/21193 | 8/1995 | WIPO . |
| 96/12955 | 5/1996 | WIPO . |

OTHER PUBLICATIONS

Eisinger, M., and Marko, O., "Selective Proliferation of Normal Human Melanocytes In Vitro in the Presence of Phorbol Ester and Cholera Toxin," *Proc. Natl. Acad. Sci. USA*, 79:2018–2022 (1982).
Wong, G. and Pawelek, J., "Melanocyte–Stimulating Hormone Promotes Activation of Pre–Existing Tyrosinase Molecules in Couldman S91 Melanoma Cells," *Nature*, 255:644–646 (1975).
Hirobe, T., "Structure and Function of Melanocytes: Microscopic Morphology and Cell Biology of Mouse Melanocytes in the Epidermis and Hair Follicle," *Histol. Histopathol.* 10:223–237 (1995).
Brady, L. and Dodson, G., "Reflections on a Peptide," *Nature*, 368: 692–693 (1994).
McLeod, S.D., et al., "Stimulation of Tyrosinase in Human Melanocytes by Pro–opiomelanocortin–Derived Peptides," *J. Endocrinology*, 146:437–447 (1995).
Nishizuka Y., "Intracellular Signaling by Hydrolysis of Phospholipids and Activation of Protein Kinase C," *Science*, 258:607–613 (1992).

Shibahara, S., et al., "Molecular Basis for the Heterogeneity of Human Tyrosinase," *Tohoku J. Exp. Med.*, 156:403–414 (1988).
Nishizuka Y., "The Molecular Heterogeneity of Protein Kinase C and its Implications for Cellular Regulation," *Nature*, 334:661–665 (1988).
Zhu, N., et al., "Systemic Gene Expression After Intravenous DNA Delivery into Adult Mice," *Science*, 261:209–211 (1993).
Takeda, A., et al., "Functional Analysis of the cDNA Encoding Human Tyrosinase Precursor," *Biochem. and Biophy. Res. Comm.*, 162(3) :984–990 (1989).
Park, H.–Y., et al., "Mechanisms of Protein Kinase C–Induced Melanogenesis in Cultured Human Melanocytes," *J. Invest. Dermatol.*, 104(4):585 (Abstract No. 186) (1995).
Li, L., et al., "High Efficiency Liposome–Mediated Transfection of the Tyrosinase Gene to Cultured Cells: A Model for the Gene Therapy of Hair Color Restoration," *In Vitro Cell. Dev. Biol.*, 30A:135–138 (1994).
Pai, J.–K, et al., "Overexpression of Protein Kinase C β1 Enhances Phospholipase D Activity and Diacylglycerol Formation in Phorbol Ester–Stimulated Rat Fibroblasts," *Proc. Natl. Acad. Sci. USA*, 88:598–602 (1991).
Choi, P.M., et al., "Overexpression of Protein Kinase C in HT29 Colon Cancer Cells Causes Growth Inhibition and Tumor Suppression," *Mol. and Cell. Biol.*, 10:4650–4657 (1990).
Ishii, H., et al., "Amelioration of Vascular Dysfunctions in Diabetic Rats by an Oral PKC β Inhibitor," *Science*, 272:728–731 (1996).
Abdel–Malek, Z., et al., "Mitogenic, Melanogenic, and cAMP Responses of Cultured Neonatal Human Melanocytes to Commonly Used Mitogens," *J. Cell. Physiol.*, 150:416–425 (1992).
Allan, A.E., et al., "Topically Applied Diacylglycerols Increase Pigmentation in Guinea Pig Skin," *J. Invest. Dermatol.*, 105(5):687–692 (1995).
Bouchard, B., et al., "Induction of Pigmentation in Mouse Fibroblasts by Expression of Human Tyrosinase cDNA," *J. Exp. Med.*, 169:2029–2042 (1989).
Jiménez, M., et al., "Tyrosinases from Two Different Loci Are Expressed by Normal and by Transformed Melanocytes," *J. Biol. Chem.*, 266(2):1147–1156 (1991).
Jackson, I.J., et al., "A Second Tyrosinase–Related Protein, TRP–2, Maps to and is Mutated at the Mouse *slaty* Locus," *EMBO J.*, 11(2):527–535 (1992).

(List continued on next page.)

*Primary Examiner*—Robert A. Wax
*Assistant Examiner*—Einar Stoce
*Attorney, Agent, or Firm*—Hamilton, Brook, Smith & Reynolds, P.C.

[57] ABSTRACT

Methods are described whereby vertebrate skin, hair, wool or fur may be lightened, or darkened, in color by administration of a substance, e.g., peptide, antibody, antibody fragment or DNA sequence encoding a peptide, that modulates the protein kinase C-beta-mediated activation of tyrosinase, the rate-limiting enzyme in melanogenesis.

19 Claims, 1 Drawing Sheet

OTHER PUBLICATIONS

Cohen, T., et al., "Nucleotide Sequence of the cDNA Encoding Human Tyrosinase–Related Protein," *Nucleic Acids Res.*, 18(9):2807–2808 (1990).

Orlow, S.J., et al., "High–Molecular–Weight Forms of Tyrosinase and the Tyrosinase–Related Proteins: Evidence for a Melanogenic Complex," *Soc. Invest. Dermatol.*, 103(2):196–201 (1994).

Park, H–Y., et al. "Cell–Specific and Age–Dependent Expression of Protein Kinases in Human Skin–Derived Cells," *Clinical Res.*, 30(2):148A (Abstract) (1991).

Bouchard, B., et al., "Production and Characterization of Antibodies Against Human Tyrosinase," *Soc. Invest. Dermat.*, 102(3):291–295 (1994).

Pomerantz, S., et al., "The Tyrosine Hydroxylase Activity of Mammalian Tyrosinase," *J. Biol. Chem.*, 241(1):161–168 (1966).

Gordon, P.R. and Gilchrest, B.A., "Human Melanogenesis is Stimulated by Diacylglycerol," *Soc. Invest. Dermatol.*, 93(5):700–702 (1989).

Jameson, B.A., et al., "A Rationally Designed CD4 Analogue Inhibits Experimental Allergic Encephalomyelitis," *Nature*, 368:744–746 (1994).

Park, H–Y. and Gilchrest, B.A., "Protein Kinase C: Biochemical Characteristics and Role in Melanocyte Biology," *J. Dermatol Science*, 6:185–193 (1993).

Yarosh, D., et al., "Localization of Liposomes Containing a DNA Repair Enzyme in Murine Skin," *Soc. Invest. Dermatol*, 103(4):461–468 (1994).

Caplan, N.J., et al., "Liposome–Mediated CFTR Gene Transfer to the Nasal Epithelium of Patients with Cystic Fibrosis," *Nature Med.*, 1(1):39–46 (1995).

Park, H–Y., et al., "The $\beta$ Isoform of Protein Kinase C Stimulates Human Melanogenesis by Activating Tyrosinase in Pigment Cells," *J. Biol. Chem.*, 268(16):11742–11749 (1993).

Eller, M.S., et al., "DNA Damage and Melanogenesis," *Nature*, 372:413–414 (1994).

Li, L. and Hoffman, R.M., "The Feasibility of Targeted Selective Gene Therapy of the Hair Follicle," *Nature Med.*, 1(7):705–706 (1995).

Kwon, B.S., et al., "Isolation and Sequence of a cDNA Clone for Human Tyrosinase that Maps at the Mouse c–Albino Locus," *Proc. Natl. Acad. Sci. USA*, 84:7473–7477 (1987).

Park, H–Y., et al., "Protein Kinase C Stimulates Melanogenesis Through Phosphorylation of Tyrosinase," *J. Invest. Derm.*, 100(4):495 (Abstract No. 37) (1993).

Park, H–Y., et al., "Protein Kinase C–$\beta$ Activates Tyrosinase," *J. Invest. Derm.*, 100(4), (Abstract No. 607) (1993).

Hearing, V.J. and King, R.A., "Determinants of Skin Color: Melanocytes and Melanization," In *Pigmentation and Pigmentary Disorders* Levine, N. (ed), CRC Press, Boca Raton, FL; pp. 297–336 (1993).

Park, H–Y., et al., "$\alpha$–Melanocyte Stimulating Hormone–Induced Pigmentation is Blocked by Depletion of Protein Kinase C," *Exper. Cell Res.*, 227:70–79 (1996).

Park, H–Y., et al., "Reduction of Melanogenic Activity and Responsiveness to a $\alpha$–Melanocyte–Stimulating Hormone During Serial Passage of Melanoma Cells," *J. Cutaneous Med. and Surgery*, 1(1):4–9 (1996).

Park, H–Y., "Depletion of Protein Kinase C Blocks Alpha––Melanocyte Stimulating Hormone–Induced Melanogenesis," *Clinical Research*, 40(2):59A (Abstract) (1992).

Park, H–Y, et al., "The $\beta$ Isoform of Protein Kinase C Stimulates Human Melanogenesis by Activating Tyrosinase in Pigment Cells," *J. Biol. Chem.*, 268(16) :11742–11749 (1993).

Naeyaert, J.M., et al., "Pigment Content of Cultured Human Melanocytes Does Not Correlate with Tyrosinase Message Level," *Chemical Abstracts*, 120(25):320141 (Abstract No. 320132z) (1994).

Eisinger, M. and Marko, O., "Selective Proliferation of Normal Human Melanocytes In Vitro in the Presence of Phorol Ester and Cholera Toxin," *Biological Abstracts*, 83 (Abstract No. 168663) (1982).

Gordon, P.R. and Gilchrest, B.A., "Human Melanogenesis is Stimulated by Diacylglycerol," *Biological Abstracts*, 90 (Abstract No. 4743) (1989).

Park, H–Y, et al., "$\alpha$–Melanocyte Stimulating Hormone–Induced Pigmentation is Blocked by Depletion of Protein Kinase C," *Biological Abstracts*, 125(19) (Abstract No. 238942h) (1996).

International Search Report, International Application No.: PCT/US97/04752, Mailed: Aug. 18, 1997.

Yaar, M., et al., "The trk Family of Receptors Mediates Nerve Growth Factor and Neurotrophin–3 Effects in Melanocytes," *J. Clin. Investigation*, 94(4):1550–1562 (1994).

Lapchak, P.A., "Nerve Growth Factor Pharmacology: Application to the Treatment of Cholinergic Neurodegeneration in Alzheimer's Disease," *Exp. Neurology*, 124:16–20 (1993).

Chintamaneni, C.D., et al., "A single base insertion in the putative transmembrane domain of the tyrosinase gene as a cause for tyrosinase–negative oculocutaneous albinism," *Proc. Natl. Acad. Sci. USA* 88:5272–5276 (1991).

Tamaoki, T., et al.,"Staurosporine, A Potent Inhibitor of Phospholipid/Ca++Dependent Protein Kinase" *Biochemical and Biophysical Research Communications*, 135(2):397–402 (1986).

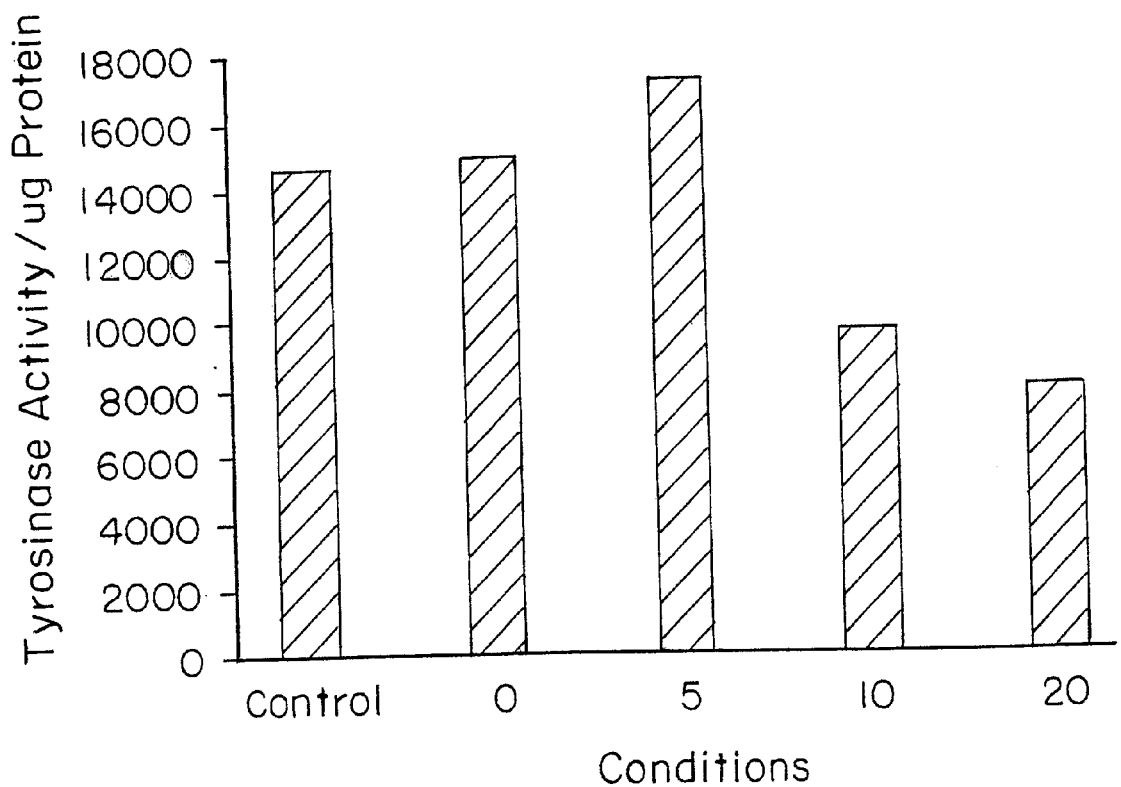
FIGURE

SEQUENCE LISTING

<160> NUMBER OF SEQ ID NOS: 4

<210> SEQ ID NO 1
<211> LENGTH: 23
<212> TYPE: PRT
<213> ORGANISM: Homo sapiens

<400> SEQUENCE: 1

Gln Leu Pro Glu Glu Lys Gln Pro Leu Leu Met Glu Lys Glu Tyr His
1               5                   10                  15
Ser Leu Tyr Gln Ser His Leu
            20

<210> SEQ ID NO 2
<211> LENGTH: 6
<212> TYPE: PRT
<213> ORGANISM: Homo sapiens

<400> SEQUENCE: 2

Gln Leu Pro Glu Glu Lys
1               5

<210> SEQ ID NO 3
<211> LENGTH: 7
<212> TYPE: PRT
<213> ORGANISM: Homo sapiens

<400> SEQUENCE: 3

Gln Pro Leu Leu Met Glu Lys
1               5

<210> SEQ ID NO 4
<211> LENGTH: 11
<212> TYPE: PRT
<213> ORGANISM: Homo sapiens

<400> SEQUENCE: 4

Glu Asp Tyr His Ser Leu Tyr Gln Ser His Leu
1               5                   10

METHODS OF MODULATING MELANIN SYNTHESIS

RELATED APPLICATIONS

This application is a continuation of PCT/US97/04752 filed Mar. 27, 1997, which is a continuation-in-part of prior Ser. No. 08/623,364 filed Mar. 28, 1996, the teachings of which are hereby incorporated herein by reference in their entirety.

BACKGROUND OF THE INVENTION

Cosmetically displeasing hyperpigmentation of the skin, due to increased melanin content in melanocytes, and the surrounding keratinocytes can result from burns, or other injuries, and is also a characteristic of some birthmarks and some skin diseases. Currently, correction of these conditions often encompasses painful grafting to replace burned skin, or surgery, e.g., laser surgery or excision of the area of unwanted coloration.

Sometimes, it is also desirable to lighten hair, wool or fur. For example, some people lighten, or "bleach" facial or scalp hair for cosmetic purposes. Some currently available methods for bleaching hair typically use harsh chemicals that can irritate sensitive skin surrounding the hair and damage the hair shaft, sometimes to the point of breakage. Furthermore, only the top of the hair shaft is affected by such treatment, leaving dark roots at, and below, the skin surface. These dark roots eventually grow out, necessitating repeated applications of these bleaching chemicals.

It would be advantageous to have available methods of decreasing, or suppressing, pigmentation in skin, hair, wool or fur without the need for surgical procedures or harsh chemicals.

SUMMARY OF THE INVENTION

The present invention is based on Applicants' discovery that activation of tyrosinase, the rate-limiting enzyme in melanogenesis, results from the protein kinase C-beta (also referred to herein as PKC-$\beta$) -mediated phosphorylation of serine and threonine residues of the cytoplasmic domain of tyrosinase.

Tyrosinase is found exclusively in melanocytes (pigment cells). These cells are located in the basal layer of the epidermis and in the hair bulb. Melanin pigment is deposited in melanocyte-specific organelles called melanosomes that are then transferred from the melanocyte to surrounding keratinocytes so that the pigment is widely dispersed through the epidermis (outer layer) of the skin or the hair shaft. The color (pigmentation) of vertebrate skin, hair, wool and fur is determined largely by its melanin pigment content.

Tyrosinase, a copper-binding transmembrane glycoprotein localized in the melanosome, is the principal and rate limiting enzyme in melanin synthesis by virtue of its ability to catalyze tyrosine hydroxylation and subsequent oxidation, the first two reactions in the biosynthetic sequence. Transfection experiments have established that tyrosinase alone enables otherwise non-melanogenic cells to produce melanin pigment (Bouchard, B, et al., *J. Exp. Med.*, 169:2029–2042 (1989)); and cloning of the human and murine tyrosinase genes has permitted mapping of numerous mutations responsible for albinism, a heritable loss of ability to pigment (King, R. A., et al., PIGMENTATION AND PIGMENTARY DISORDERS, Levine, N., (ed.), CRC Press, Boca Raton. Fla., pp. 297–336 (1993)).

Several other enzymes are known to participate in melanin biosynthesis. These include Tyrosinase Related Proteins 1 and 2 (TRP 1 and TRP 2) (Cohen, T., et al., *Nucleic Acids Res.* 18:2807–2808 (1990); Jackson, I. J., et al., EMBO J., 11:327–535 (1992)). As their names imply, the TRPs are structurally related to tyrosinase. In particular, the genes are homologous in the copper binding site and cysteine-rich domains, areas that are important for their structure and function (Hearing, V. J. and King, R. A., PIGMENTATION AND PIGMENTARY DISORDERS, Levine, N., (ed.), CRC Press, Boca Raton. Fla., pp. 3–32 (1993) ). The specific function of the TRPs are not known. However, recent data suggest that tyrosinase, TRP 1 and TRP 2 interact in vivo to form a complex, and that within this complex tyrosinase activity is diminished, suggesting that the TRPs may act as inhibitors of tyrosinase activity (Orlow, S. J., et al., J. Invest. Dermatol., 103:196–201 (1994)).

In particular, Applicants have identified the specific serine residues in the cytoplasmic domain of tyrosinase that are phosphorylated by PKC-$\beta$. As a result of Applicants' discovery, methods are provided to modulate the activation of tyrosinase in vertebrate melanocytes. Modulate, as defined herein, means to alter the activation of tyrosinase either by preventing or inhibiting (decreasing) activation, or by enhancing or sustaining activation. For example, the activation of tyrosinase can be modulated by substantially decreasing, or completely blocking the PKC-$\beta$-mediated phosphorylation of tyrosinase, resulting in a decrease in melanogenesis. Conversely, tyrosinase activation can be modulated by enhancing activation, e.g., by facilitating the phosphorylation of tyrosinase, or sustaining activation, e.g., by preventing dephosphorylation of tyrosinase, resulting in an increase in melanogenesis.

Also provided are methods of altering pigmentation in vertebrate skin, hair, wool or fur as a result of modulating the activation of tyrosinase in melanocytes contained in the epidermis and in hair, wool and fur bulbs. As used herein, the term epidermal melanocytes refers to melanocytes contained in the skin, and in the bulbs, or follicles of hair, wool and fur. The alteration of pigmentation, as used herein, means that pigmentation in epidermal melanocytes is either increased as a result of activation of tyrosinase which results in an increase in melanogenesis, or, alternatively, that pigmentation is decreased as a result of the inhibition of activation of tyrosinase, resulting in the decrease of melanogenesis.

One embodiment of the present invention relates to methods of preventing, or inhibiting, the activation of tyrosinase in vertebrate epidermal melanocytes. Tyrosinase is a monomeric protein with an inner domain, short transmembrane domain and a cytoplasmic domain. The cytoplasmic domain of tyrosinase contains serine residues. These serine amino acid residues are likely substrates for phosphorylation by PKC-$\beta$. As described herein, Applicants have demonstrated that serines at positions 505 and 509 of the tyosinase amino acid sequence (Shibahara, S., et al., Tohoku J. Exp. Med., 156:403–411 (1988)) are sites of PKC-$\beta$-mediated phosphorylation of tyrosinase. Inhibiting the phosphorylation of serine 505 and/or 509 prevents the activation of tyrosinase.

Inhibition of the PKC-β-mediated phosphorylation of tyrosinase prevents activation of tyrosinase in epidermal melanocytes which results in a decrease in the production of melanin pigment in melanocytes. Thus, another embodiment of the present invention relates to decreasing, or completely suppressing pigmentation in vertebrate skin, hair, wool or fur.

Conversely, enhancing or sustaining tyrosinase activation by, e.g., preventing dephosphorylation of the activated tyrosinase, sustains, or prolongs melanogenesis in epidermal melanocytes, resulting in increased pigmentation of vertebrate skin, hair, wool or fur.

In another embodiment of the present invention, methods are provided to identify a substance which decreases, or completely suppresses, pigmentation in vertebrate epidermal melanocytes. Substances, for example, peptides, that specifically interfere with the interaction, or association, of PKC-β and tyrosinase mimic the sequence/structure of tyrosinase phosphorylation sites (e.g., peptide mimics), and bind to PKC-β, thereby preventing PKC-β from phosphorylating tyrosinase, and thus, preventing tyrosinase activation.

Conversely, methods are also provided to identify a substance which increases pigmentation in vertebrate epidermal melanocytes. Substances, for example, peptides, that specifically interfere with the phosphatases involved with the dephosphorylation of tyrosinase prevent tyrosinase deactivation. Substances identified by the methods described herein are also encompassed by the present invention.

As a result of Applicants' discovery of the specific sites of phosphorylation on tyrosinase, the rate-limiting enzyme in melanogenesis, methods are now available to modulate tyrosinase activation and pigmentation in vertebrate epidermal melanocytes. Methods are now available to increase pigmentation of skin, hair, wool and fur. Specifically, methods are now available to decrease, or suppress, (partially or completely) pigmentation of the skin, hair, wool and fur without surgery or harsh chemicals.

BRIEF DESCRIPTION OF THE FIGURE

The FIGURE is a graphic representation of experimental results showing that a synthetic peptide constructed to mimic the phosphorylation site of human tyrosinase inhibits tyrosinase activity in cultured human melanocytes.

DETAILED DESCRIPTION OF THE INVENTION

The present invention is based on Applicants' finding that activation of tyrosinase, the rate-limiting enzyme in melanogenesis, results from the protein kinase C-beta (also referred to herein as PKC-β) -mediated phosphorylation of serine and threonine residues of the cytoplasmic domain of tyrosinase. Tyrosinase is a transmembrane protein localized to the melanosomes contained in melanocytes. Nucleotide sequences of cDNA clones for human tyrosinase have been reported in Shibahara, S., et al. Tohoku J. Exp. Med., 156:403–414 (1988); Chinatamaneni, C. D., et al. Proc. Natl. Acad. Sci. U.S.A., 88:5272–5276 (1991) and Kown, B. S. et al. Proc. Natl. Acad. Sci. USA, 84:7473–7477 (1987), the teachings of which are incorporated herein by reference. The putative human tyrosinase is composed approximately of 511 amino acids (Shibahara, S., et al. Tohoku J. Exp. Med., 156:403–414 (1988)). The cytoplasmic domain comprises two serine residues at the 505 and 509 positions of the amino acid sequence of Shibauhaer et al. and Chinatamanei, C. D., et al.

Tyrosinase is activated by the beta isoform of protein kinase C (PKC-beta). In the absence of PKC-beta, no melanin pigment is formed (Park, H-Y, et al., J. Biol. Chem., 268:11742–11749 (1993)). Conversely, activation of PKC-beta above basal levels increases pigmentation in cultured human melanocytes, murine melanoma cells and in guinea pig skin. PKC-beta (PKC-β) is a serine/threonine kinase and activates proteins by phosphorylation of these amino acid residues. Park, H-Y. and Gilchrest, B. A., J. Dermatol. Sci., 6:185–193 (1993)). Full length tyrosinase shows incorporation of 22p phosphase, but the inner domain alone does not, suggesting that PKC-B phosphorylates only the cytoplasmic domain (Park, H-Y., et al., J. Invest Dermatol., 104:585 Abstract 186 (1995)).

As described herein, Applicants have now demonstrated that activation of PKC-β in melanocytes leads to phosphorylation of tyrosinase, and specifically to phosphorylation of serine residues at positions 505 and 509 in the cytoplasmic domain of tyrosinase. Applicants have further demonstrated that removal of the cytoplasmic domain of tyrosinase by proteolysis prevents its phosphorylation by PKC-β. Thus, Applicants have demonstrated that preventing PKC-β-mediated phosphorylation of tyrosinase prevents activation of the rate limiting enzyme in melanogenesis and results in decreased, or completely suppressed, pigmentation in the target tissue, for example, vertebrate skin, hair, wool or fur.

Molecules or substances that specifically interfere with, or block, the interaction, or association, of PKC-β and tyrosinase can specifically inhibit, or substantially decrease the activation of tyrosinase. For example, molecules that specifically interfere with the phosphorylation of either serine residue 505 and 509, or both, can prevent tyrosinase activation. If tyrosinase is not activated, melanogenesis is significantly inhibited, resulting in decreased pigmentation, or complete suppression of pigmentation, in epidermal melanocytes.

Molecules such as proteins, peptides, antibodies and antibody fragments can interfere with the interaction between PKC-β and tyrosinase. Organic and inorganic molecules can also interfere with this interaction. Such molecules can be naturally occurring, and purified, or isolated from their natural environment, using techniques well-known to those of skill in the art. Such molecules can also be synthesized by chemical means, or recombinantly produced, also using techniques well-known to those of skill in the art.

As used herein, specific interference of the interaction between PKC-β and tyrosinase refers to the prevention, or blocking, of PKC-β-mediated phosphorylation of tyrosinase. The blocking can be complete blocking, or partial blocking, which results in the complete inhibition, or substantial reduction of melanogenesis in epidermal melanocytes. Complete inhibition of, or substantial reduction of melanogenesis in epidermal melanocytes results in decreased pigmentation, or completely suppressed pigmentation, in skin, hair, wool or fur in vertebrates.

Specifically encompassed by the present invention are peptides, or peptide fragments that mimic the sites of interaction between PKC-β and tyrosinase. These "peptide mimics" mimic the sites of PKC-β-mediated phosphorylation of tyrosinase, i.e., amino acid residues that comprise the substrate sequences of tyrosinase for PKC-β-mediated phosphorylation. The substrate sequences of tyrosinase mimics typically include a serine or threonine residue. The amino acid sequences of tyrosinase mimics include, for example, the serine residue 505 and 509, and their respective surrounding amino acid residues. These tyrosinase peptide mimics bind directly to PKC-β in a manner similar to the binding of PKC-β to tyrosinase, thereby preventing PKC-β from binding to tyrosinase and thus, preventing, reducing or completely eliminating the activation of tyrosinase and subsequent melanogenesis.

The tyrosinase mimics used in the methods described herein can be, e.g., proteins, peptides (comprised of natural and non-natural amino acids) or can be peptide analogs (comprised of peptide and non-peptide portions). Such peptide mimics can be constructed with D-isomers rather than the native L-isomers of the amino acids, to increase their resistance to proteolytic degradation within living cells. All tyrosinase mimics used in these methods have specific characteristics pertaining to biological activity. These characteristics include the ability of these mimics to bind to PKC-β and the retention of a biologically active conformation.

The tyrosinase peptide mimics used in the methods described herein include at least five amino acid residues, and generally have a sequence in the range of about ten to about thirty amino acid residues, typically having about twenty residues. However, longer mimics can be used (e.g., the length of the entire cytoplasmic domain, or up to about 60–65 amino acid residues) if they have the desired characteristics described above. Typically, one of the residues of tyrosinase peptide mimics is a serine or threonine. For example, tyrosinase mimics such as SEQ ID NO: 1 and SEQ ID NO.: 4 are especially useful in the methods described herein.

Molecules that mimic the active sites of PKC-β can also be used in the methods described herein. Such a PKC-β-mimic molecule would bind to the tyrosinase substrate sequence, but would not activate tyrosinase. However, the PKC-β mimic binding to the substrate prevents PKC-β binding to tyrosinase. Thus, the PKC-β mimic would also block the PKC-β-mediated phosphorylation of tyrosinase as a competitive antagonist, inhibiting the activation of tyrosinase and decreasing pigmentation. Such PKC-β mimics can comprise, for example, proteins, peptides, organic or inorganic molecules.

Tyrosinase mimics and PKC-β mimics can be rationally designed and synthetically produced by methods well-known to those of skill in the art, for example, as described in Jameson, B. A., et al., Nature, 368:744–746 (1994). Candidate tyrosinase mimics and PKC-β mimics can be identified and screened for biological activity (i.e., the ability to block the interaction of PKC-β with tyrosinase) using in-vitro assays well-known to those of skill in the art.

For example, as described herein, one method comprises culturing melanocytes containing tyrosinase in the presence of a radioactive label such as $^{32}$P-orthophosphate. The melanocytes can be obtained from skin biopsies, neonatal foreskins or melanoma cell lines (see, e.g., Park, H-Y. et al., J. Biol. Chem., 268:11742–11749 (1993)). The melanocytes are contacted with a phorbol ester such as tetraphorbol acetate (TPA) to activate PKC-β. Other suitable PKC-β activators known to those of skill in the art can also be used. Simultaneously, or subsequentially, the cultured melanocytes are contacted with the substance to be tested under conditions suitable for PKC-β-mediated phosphorylation of tyrosinase. Tyrosnase-containing melanosomes are then purified from the TPA-treated melanocytes and tyrosinase is isolated from the melanosomes. Isolation can be accomplished by standard laboratory techniques. In particular, isolation by immunoprecipitation with an antibody specific for tyrosinase is encompassed by the present method. The antibody can be polyclonal or monoclonal. (See e.g., Jimenez, M. et al., J. Biol. Chem., 266:147–1156 (1991); Bouchard, B. et al., J. Invest. Dermatol., 102:291–295 (1994); or EPO 679,660 A1 Feb. 11, 1995).

Immunoprecipitation assays can be performed as described in e.g., Park, H-Y. et al., J. Biol. Chem., 268:11742–11749 (1993). The amount of $^{32}$P-orthophosphate incorporated in the immunoprecipitated tyrosinase is determined using standard laboratory techniques, and the amount of $^{32}$P-orthophosphate incorporated into tyrosinase isolated from melanocytes cultured in the presence of a test substance is compared with the amount of $^{32}$P-orthophosphate incorporated into tyrosinase isolated from melanocytes cultured in the absence of a test substance. A decreased amount of $^{32}$P-orthophosphate incorporation into tyrosinase is an indication that the test substance prevents phosphorylation of (i.e., activation of) tyrosinase. As the test substance prevents activation of tyrosinase, and tyrosinase is essential for melanogenesis and pigmentation, pigmentation in vertebrate epidermal melanocytes is completely inhibited or substantially decreased.

Alternatively, tyrosinase activity can be directly measured using other well-known laboratory techniques. For example, Pomerantz, S. H. describes an assay to measure tyrosinase activity (J. Biol. Chem., 241:161–168 (1966), the teachings of which are incorporated by reference). In brief, $5 \times 10^6$ cells are briefly sonicated in 80 mM $PO_4^{2-}$ (pH 6.8) containing 1% Triton X-100, and tyrosinase is extracted for 60 minutes at 4° C. 10–50 g of cellular protein are incubated with 250 nM L-tyrosine, 25 nM L-deoxyphenylalanine, 12.5 µg of chloramphenicol, and 5 µCi of L-[3,5-$^3$H] tyrosine for 30–60 minutes at 37° C. The reaction is stopped by addition of 500 µl of 10% trichloroacetic acid containing 0.2% BSA. Trichloroacetic acid-soluble material is reacted with Norit A, and released $^3H_2O$ is measured using a scintillation counter. The activity is expressed as counts/minute $^3H_2O$ released/µg protein/h minus the nonspecific incorporation of radioactivity, determined by using lysate boiled for 30 minutes (background).

Additionally, the melanin content of melanocytes can be measured directly, as described, for example, in Gordon, P. R. and Gilchrest, B. A., J. Invest. Dermatol., 93:700–702 (1989), the teachings of which are also incorporated herein by reference. Briefly, human melanoma cells are cultured under standard laboratory conditions. $1 \times 10^5$ cells are routinely used to measure melanin content. Cells are spun at 2,500 rpm for 15 minutes and the resulting pellet is dissolved in 0.5 ml of 1 N NaOH. Melanin concentration is calculated by $OD_{475}$ and comparison with a standard curve of synthetic melanin.

Tyrosinase mimics and PKC-β mimics that exhibit activity in vitro can be further tested in-vivo, for example, by topical application to guinea pig skin or hair, as described in Eller, M. et al., Nature, 372:413–414 (1994) or Allen et al., J. Invest. Dermatol., (1995), the teachings of which are incorporated herein by reference.

Conversely, Applicants' discovery regarding PKC-β activation of tyrosinase, the rate limiting enzyme in melanogenesis, provides methods of increasing synthesis of melanin and hence darkening of skin, hair, wool or fur. Methods are also provided herein to enhance, or to maintain, the steady state level of phosphorylation of tyrosinase by PKC-β as a result of blocking the dephosphorylation of serine and threonine residues of the cytoplasmic domain of tyrosinase by providing a false substrate for the relevant phosphorylase in the cells.

Specifically, the rate of melanin synthesis in melanocytes is known to be determined by the state of activation or tyrosinase. This activation state is a dynamic equilibrium between activation (phosphorylation) of the enzyme and deactivation (dephosphorylation) of the enzyme that is associated with the intracellular melanosomes. Phosphorylation is mediated by PKC-β and dephosphorylation is mediated by one or more phosphatases. It is reasonable to assume that different phosphatases are responsible for dephosphorylating different PKC-β substrates, as would be required in a situation in which multiple PKC substrates must be regulated independently for normal cell function.

A peptide sequence specific for the catalytic domain of the phosphatase responsible for dephosphorylation of PKC-β-activated tyrosinase can be constructed and delivered to melanocytes in the skin, hair, wool or fur or any additional site where increased melanogenesis is desired. This "false substrate" for the phosphatase competes with the phosphorylated site on tyrosinase for its active site and thus reduces the availability of the phosphatase to the physiologic substrate, tyrosinase. This method can be used when increased melanin content is desired, e.g., in areas of post-inflammatory hypopigmentation of the skin as commonly occurs in patients with low grade eczematous dermatitis, or to darken human hair shade, or the color of animal fur or wool.

Thus, providing substances to cells that modulate the activation of tyrosinase can modulate the synthesis of melanin in epidermal melanocytes. Specifically, providing tyrosinase peptide mimics to cells or tissues can result in competitive interaction of the added peptide with PKC-β, decreasing the availability of PKC-β to interact with its normal intracellular substrate, in this instance the cytoplasmic domain of tyrosinase contained within the melanocyte. Such a substrate sequence can interact specifically or preferentially with PKC-β rather than with other PKC isomers because the other PKC isomers do not activate tyrosinase protein. Although PKC isomers are found ubiquitously in cells and tissues, and are known to mediate a wide variety of critical cellular functions, a substrate sequence specific for PKC-β acts preferentially on the melanogenic pathway in melanocytes because PKC-β is minimally expressed in keratinocytes or fibroblasts, the other major cell types in the skin (Park, H-Y. et al., Clin. Res., 39:148A (1991)).

Furthermore, it is known that human melanoma cell lines completely lacking PKC-β are indistinguishable from parental lines expressing this PKC isoform, except for the fact that they lack melanin pigment (Park, H. E. et al., J. Biol. Chem., 268(16):11742–11749 (1993)). This strongly suggests that PKC-β does not serve any other major function in melanocyte/melanoma cells, aside from its role in melanogenesis.

The methods of the present invention can be used to alter pigmentation in vertebrate melanocytes via modulation of the activation of tyrosinase. Specifically, the methods described herein can be used to decrease, or completely suppress, pigmentation in vertebrate skin, hair, wool or fur. These methods comprise contacting, epidermal cells in such a manner that the substance enter the cell, including basal layer melanocytes, (e.g., introducing into, delivering to, or administering to) with an effective amount of a substance which of decreases, or suppresses, pigmentation by decreasing or inhibiting the activation of tyrosinase in melanocytes. For example, the substance can be contained in a physiologically compatible composition which is topically applied to the skin, or skin surrounding the hair, wool or fur bulbs.

Conversely, the methods of the present invention can also be used to increase pigmentation in vertebrate skin, hair, wool or fur. These methods comprise contacting, or delivering to, epidermal melanocytes (melanocytes located in the skin or hair, wool or fur bulbs) with an effective amount of a substance which increases pigmentation by enhancing or sustaining the activation of melanocytes in vertebrates.

An effective amount of such an identified substance is an amount effective to modulate (e.g., substantially reduce, or completely inhibit, or substantially enhance or sustain) PKC-β-mediated phosphorylation of tyrosinase in epidermal melanocytes. The modulation of tyrosinase phosphorylation in melanocytes can be evaluated using the methods described herein.

Various delivery systems suitable for use in the present invention are known to those of skill in the art and can be used to administer effective amounts of substances, such as tyrosinase peptide mimics, to inhibit activation of tyrosinase in melanocytes. For example, protein encapsulation in liposomes, microparticles, or microcapsules; expression by recombinant cells, receptor-mediated endocytosis, construction of a naturally-occurring or pseudo-ligand encoding nucleic acid as part of a retroviral or other vector can be used.

In one embodiment, a liposome preparation can be used. The liposome preparation can be comprised of any liposome which penetrates the stratum corneum and fuses with the cell membrane, resulting in delivery of the contents of the liposome into the cell. Liposomes can be prepared by methods well-known to those of skill in the art. For example, liposomes such as those described in U.S. Pat. No. 5,077,211; U.S. Pat. No. 4,621,023; U.S. Pat. No. 4,880,635 or U.S. Pat. No. 5,147,652 can be used. See also, Yarosh, D., et al., J. Invest. Dermatol., 103(4):461–468 (1994) or Caplen, N. J., et al., Nature Med., 1(1):39–46 (1995).

The liposomes can specifically target the appropriate cells (e.g., epidermal melanocytes). For example, a membrane marker preferentially expressed on melanocytes, such as melanocyte stimulating hormone (MSH) receptor, can be incorporated into a liposome containing a peptide mimic that prevents the activation of tyrosinase. Liposomes can also specifically target and deliver substances to the hair follicles, as described below in Li, L. and Hoffman, R. M., et al., the teachings of which are incorporated herein by reference. Such a liposome delivery system can also be used to deliver substances to wool and fur bulbs.

For example, a peptide mimic, or a DNA construct encoding a peptide mimic, can be encapsulated into a liposome by techniques well known to those of skill in the art. The DNA construct will comprise the DNA sequence encoding the peptide and other nucleic acid sequences necessary for the expression of the peptide in vertebrate cells. (See, for example, Li, L. and Hoffman, R. M., Nature Med., 1:705–706 (1995) or Yarosh, D. et al., J. Invest.Dermatol., 103:461–468 (1994)). The liposome-DNA construct, or liposome-peptide composition (containing the peptide mimic) can be administered to the vertebrate, for example, by topical application to the skin, hair, wool or fur, or to the skin surrounding the hair, wool or fur bulb. The liposome-DNA construct, or liposome-peptide composition contacts the melanocytes, with the result that the contents of the liposome (DNA or peptide) are introduced into the melanocytes in which the peptide mimic is expressed, or released, resulting in modulation of tyrosinase activation.

Substances used in the present methods can also be directly administered in a physiologically compatible carrier. For example, peptides of the size required to competitively inhibit PKC-β phosphorylation of tyrosinase are sufficiently small to permit their transepidermal delivery to melanocytes in the epidermis and hair, wool or fur bulb using existing technology. The peptide can be admixed in a topical carrier such as a gel, an ointment, a lotion, a cream, or a foam, or a shampoo and will include such carriers as water, glycerol, alcohol, propylene glycol, fatty alcohols, triglycerides, fatty acid esters, or mineral oils. Other possible topical carriers include, e.g., liquid petrolatum, isopropyl palmitate, polyethylene glycol, ethanol (95%), polyoxyethylene monolauriate (5%) in water, sodium lauryl sulfate (5%) in water. Other materials such as anti-oxidants, humectants, viscosity stabilizers, and similar agents may be added as necessary.

In addition, in certain instances, it is expected that the substances can be disposed within devices placed upon, in, or under the skin. Such devices include transdermal patches, implants, and injections which release the substances in such a manner as to contact the skin or hair follicle either by passive or active release mechanisms.

The delivery vehicle can also contain perfumes, colorants, stabilizers, sunscreens, or other ingredients. The substance can be applied, for example, topically to the epidermis at regular intervals, such as once or twice daily, in a suitable vehicle and at an effective concentration.

An effective amount of a mimic substance that modulates the activation of tyrosinase can be administered to a vertebrate, including a human, using any of the above-described methods. The actual preferred amounts of substance to be administered will vary according to the specific mimic being utilized, the particular compositions formulated, the mode of application, and the particular sites and vertebrate being treated. The concentration of the mimic effective to prevent activation of tyrosinase, in a vertebrate, such as a human, can be determined using known, conventional pharmacological protocols.

The present invention also encompasses methods of identifying a substance capable of altering pigmentation in vertebrate epidermal melanocytes, and the substances identified by these methods. These methods identify substances based on the effect the substance has on the protein kinase-C-β-mediated activation of tyrosinase in epidermal melanocytes.

For example, vertebrate epidermal melanocytes are grown in culture under conditions suitable for maintaining the growth and viability of the melanocytes. The substance to be tested (i.e., the test-substance) is then introduced into the culture and thus, into the cultured cells. The culture containing the test substance is maintained under conditions suitable for the substance to affect tyrosinase activity, e.g., to inhibit protein kinase-C-β-mediated phosphorylation of tyrosinase. Control cultures of melanocytes are also maintained under similar conditions but without the presence of substance to be tested. After a suitable period of time, the melanocytes are removed, or isolated, from the culture, e.g., by centrifugation, and tyrosinase is isolated from the melanocytes, e.g., by immunoprecipitation with tyrosinase-specific antibody. Immunoprecipitation can also be accomplished using a specific antibody that recognizes a fragment of tyrosinase, e.g., the tyrosinase cytoplasmic domain.

Phosphorylation of tyrosinase is then evaluated. Evaluation of phosphorylated typically encompasses quantifying the amount of, or the magnitude of, phosphorylation that has occurred while the melanocytes were cultured with the test-substance. A standard method of quantification is determining the amount of radiolabeled phosphate incorporated into tyrosinase, for example, $^{32}$P-orthophosphate. Phosphorylation of tyrosinase isolated from melanocytes cultured in the presence of test substance is then compared to the phosphorylation of tyrosinase isolated from melanocytes cultured without test substance. If the substance has the effect of inhibiting protein kinase C-β-mediated phosphorylation of tyrosinase, then the amount of phosphorylation of tyrosinase isolated from cultured melanocytes grown in the presence of the test substance will be less than the amount of phosphorylation of tyrosinase isolated from control melanocytes.

The present method can also be used to identify a substance that has the effect of increasing pigmentation in vertebrate epidermal melanocytes. Such substances would have the effect of enhancing the phosphorylation of or sustaining the phosphorylated state of tyrosinase. The steps of the method are similar to the above discussed method, except that the test substance possessed the desired characteristics of enhancing phosphorylation, the extent of phosphorylation of tyrosinase isolated from melanocytes cultured in the presence of the test substance is greater than the extent of phosphorylation of tyrosinase isolated from melanocytes cultured without test substance. To determine if a test substance had the effect of sustaining or prolonging the state of phosphorylation of tyrosinase (thus, sustaining or prolonging the activation of tyrosinase), the melanocyte cultures can be maintained with or without test substance for prolonged periods of time prior to isolating melanocytes and evaluating the phosphorylation of tyrosinase isolated from the melanocytes.

Substances identified by these in vitro methods can be further tested in vivo, for example, in guinea pigs, as described in Eller, M. S. et al., Nature, 372:413–414 (1944), the teachings of which are incorporated herein by reference. Substances that are effective in vivo can be used in the methods of altering pigmentation of vertebrate epidermal melanocytes as described above.

The following examples more specifically illustrate the invention and are not intended to be limiting in any way.

EXAMPLE 1
Protein Kinase C-beta Phosphorylates Tyrosinase

To examine if only PKC-β, but not other isoforms, phosphorylates tyrosinase in vivo, melanocytes which express PKC-β and non-pigmented-MM4 human melanoma cells that comparably express tyrosinase, but lack the expression of PKC-β, were preincubated with $^{32}$P-orthophosphate for 90 minutes. (J. Invest. Derm., Vol. 100, No.4: Abst. #37 (April 1993). PKC was activated by treating cells with $10^{-7}$M TPA, a well known activator of all PKC isoforms, for 30 minutes. Control cells received vehicle only. Subsequently, tyrosinase was immunoprecipitated using a polyclonal antibody against human tyrosinase and incorporation of $^{32}$P-orthophosphate into tyrosinase was visualized by autoradiography. Tyrosinase was only phosphorylated in TPA-treated melanocytes that express PKC-β, suggesting that only PKC-β, but not other PKC isoforms, can phosphorylate tyrosinase in vivo.

EXAMPLE 2
Tyrosinase Activity is Up-Regulated by Phosphorylation

To determine whether the activity of tyrosinase can be up-regulated by phosphorylation, purified mushroom tyrosinase was pre-incubated with purified activated PKC-β (Park, H-Y. et al., J. Invest Dermatol., 100:607 (1993) and Park, H-Y. et al., J. Biol. Chem., 268:11742–11749 (1993)). Subsequently tyrosinase activity was visualized by separating tyrosinase and PKC-β in a non-denaturing 7.5% acrylamide gel-electrophoresis, followed by reaction with L-dopa. A brown colored band (melanin) appears where tyrosinase migrates, its intensity corresponding to enzymatic activity. Purified tyrosinase alone showed some activity and the activity increased more than 10 fold when tyrosinase was pre-incubated with purified activated PKC-β. This increase is not due to a possible interaction between PKC-β and L-dopa since PKC-β alone did not react with L-dopa. These data clearly show that direct phosphorylation of tyrosinase by PKC-β leads to activation of the enzyme.

EXAMPLE 3
Protein Kinase C-beta Phosphorlylates the Cytoplasmic Domain of Tyrosinase The amino acid sequence of human tyrosinase has been previously reported. Tyrosinase has two serine residues at positions 505 and 509 in cytoplasmic domain (Shibahara, S., et al. Tohoku J. Exp. Med., 156:403–414 (1988). Approximately 90% of the tyrosinase protein is inside melanosomes, membrane-bound organelles within melanocytes in which melanin pigment is synthesized and deposited. PKC-β normally resides in the cytoplasm. To examine if only the cytoplasmic domain of tyrosinase is phosphorylated by PKC, melanocyte cultures were preincubated with $^{32}$P-orthophosphate, PKC was activated by treating with $10^{-7}$M TPA for 60 minutes, and the melanosomes (which contain tyrosinase) were purified using sucrose gradient centrifugation.

Purified melanosomes were divided into two groups: one group remained untreated as a control and the other group was treated with 0.25% trypsin for 60 minutes at 37° C. to release the cytoplasmic domain. Subsequently, trypsin-treated and untreated tyrosinase (full-length) was extracted from melanosomes by incubating in 0.1% Triton X-100 for 60 minutes and treated or untreated tyrosinase was immunoprecipitated using an polyclonal antibody specifically reacting against the inner (intra-melanosomal) domain or a polyclonal antibody against the full length tyrosinase respectively.

$^{32}$P-orthophosphate was incorporated only into untreated or full length tyrosinase (Park, H-Y., et al., J. Invest. Dermatol., 1041, 585 Abstract 186 (April 1995)). Trypsin-treated tyrosinase, lacking the cytoplasmic domain, failed to show incorporation of $^{32}$P-orthophosphate, demonstrating that only the cytoplasmic domain is phosphorylated by PKC. In a parallel experiment, melanocyte cultures were processed as above except that phosphorylation of tyrosinase was done in the absence of radiolabeled phosphate. Immunoblot analysis with untreated and trypsin-treated tyrosinase confirmed that a comparable amount of tyrosinase was immunoprecipitated using two different antibodies.

EXAMPLE 4
Protein Kinase C-beta Phosphorylates Serine and Threonine Residues

To examine if both serine and threonine residues are phosphorylated by PKC, a known serine/threonine kinase, tyrosinase was phosphorylated in vivo by preincubation of melanocytes with $^{32}$P-orthophosphate, followed by activation of PKC with TPA, as described in Example 1. Subsequently, tyrosinase was immunoprecipitated, electroeluted from the gel and subjected to a full hydrolysis. Radiolabeled amino acids were separated using two-dimensional thin-layer chromatography using standard techniques, and mapped against unlabeled and phosphorylated serine, threonine and tyrosine standards.

Results showed that >90% of the radiolabeled phosphate was associated with serine. Radiolabeled phosphate associated with tyrosine was not detected. These data further demonstrate that tyrosinase is phosphorylated through the PKC-dependent pathway and that serine residues are preferentially phosphorylated.

EXAMPLE 5
Serines 505 and 509 are Phosphorylated

To identify the exact serine or threonine residues predominantly phosphorylated by PKC-β, tyrosinase was labeled with $^{32}$P-orthophosphate by incubating melanocytes with radiolabeled phosphate and activating PKC. Subsequently melanosomes were purified and full length tyrosinase was immunoprecipitated. Tyrosinase was then treated with trypsin, then with thermolysin. Since only the cytoplasmic domain is phosphorylated, digestion of full length tyrosinase should generate only phosphorylated cytoplasmic domain.

Based on the amino acid sequence of human tyrosinase by Sibahara, it was predicted that three fragments will be generated when the cytoplasmic domain of human tyrosinase is digested with trypsin. Synthetic peptides were made with or without a phosphate group on the serine residues. In three independent experiments, all of the radiolabled phosphate was mapped to synthetic peptide 3, indicating that both serines residues are phosphorylated by PKC-β.

As shown in Table I and the FIGURE, tyrosinase activity in cultured human melanocytes is inhibited by more than 50% in cultures treated with 20 µg/dish, equivalent to 2 µg/ml, of the synthetic peptide constructed to mimic the phosphorylation site on human tyrosinase. Approximately 40% inhibition was observed at the next lower dose of 1 µg/ml

EXAMPLE 7
Protein Kinase C-beta Interaction with TRP 1 and TRP 2

To investigate whether PKC regulates other melanogenic proteins such as tyrosinase related proteins (TPR 1 and TPR 2), melanocytes were treated with $10^{-7}M$ TPA for 2 weeks, a condition known to deplete PKC, and TRP 1 and TRP 2 protein levels were determined using immunoblot analysis with specific antibodies. PKC depletion had no effect on TPR 1, but the level of the glycosylated mature form of TRP 2 (80 kd) was reduced by 50–70%. The 65 kd non-glycosylated TRP 2 precursor was unaffected by depletion of PKC. To confirm that indeed only the glycosylated TRP 2 is affected, melanocytes were treated with TPA for 2 weeks and labeled with $^3$H-glycosamine. TRP 1 and TRP 2 were immunoprecipitated and incorporation of $^3$H-glycosamine into these proteins was examined. PKC depletion did not affect either the glycosylated or non-glycosylated form of TPR 1, but $^3$H-glycosamine incorporation into TRP 2 was reduced by >50%. Together these results suggest that PKC regulates melanogenesis by preferentially phosphorylating serine residues on the cytoplasmic domain of tyrosinase and by regulating the level of mature TRP 2.

```
                Cytoplasmic Domain of Tyrosinase

Gln-Leu-Pro-Glu-Glu-Lys-Gln-Pro-Leu-Leu-Met-Glu-Lys-Glu-    (SEQ ID NO: 1)

Tyr-His-(Ser)505-Leu-Tyr-Gln-(Ser)509-His-Leu

|
                         ↓   Trypsin

Fragment 1: Gln-Leu-Pro-Glu-Glu-Lys                         (SEQ ID NO: 2)

Fragment 2: Gln-Pro-Leu-Leu-Met-Glu-Lys                     (SEQ ID NO: 3)

Fragment 3: Glu-Asp-Tyr-His-(Ser)505-Leu-Tyr-Gln-(Ser)509-  (SEQ ID NO: 4)
            His-Leu Synthetic Peptides:

Peptide 1:: Glu-Asp-Tyr-His-p(Ser)505-Leu-Tyr-Gln-          (SEQ ID NO: 4)
            (Ser)509-His-Leu Peptide 2:: Glu-Asp-Tyr-His-(Ser)505-Leu-Tyr-Gln-           (SEQ ID NO: 4)
            p(Ser)509-His-Leu Peptide 3:: Glu-Asp-Tyr-His-p(Ser)505-Leu-Tyr-Gln-          (SEQ ID NO: 4)
            p(Ser)509-His-Leu
```

EXAMPLE 6
Synthetic Peptide Inhibits Tyrosinase Activity

Paired cultures of human melanocytes were either untreated or treated with 5, 10 or 20 µg/dish of synthetic peptide whose sequence is identical to the part of human tyrosinase containing serines residues at amino acid positions 505 and 509. The specific sequence of the synthetic peptide is Glu-Asp-Tyr-His-(Ser)$_{505}$-Leu-Tyr-Gln-(Ser)$_{509}$-His-Leu (SEQ ID NO: 4). The synthetic peptide was pretreated with 10 µl of Lipofectamine to enhance delivery into the cells. Control designates no treatment and 0 designates Lipofectamine alone. Melanocytes were exposed to Lipofectamine treated synthetic peptides for 22 hours, harvested and tyrosinase activity was determined.

TABLE I

|  | Tyr Act/ µg Protein | CPM 1 | CPM 2 | CPM neg1 | CPM neg2 |
|---|---|---|---|---|---|
| Control | 14679.2 | 118490 | 119159 | 50443 | 40414 |
| 0 | 14807.4 | 126917 | 119698 | 50248 | 48203 |
| 5 | 17152.6 | 148889 | 119059 | 47579 | 48843 |
| 10 | 9536.9 | 96566 | 93442 | 46135 | 48504 |
| 20 | 7811.3 | 90265 | 84051 | 46312 | 49891 |

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of reducing activation of tyrosinase in vertebrate epidermal melanocytes comprising introducing into the melanocytes a tyrosinase phosphorylation site mimic which reduces phosphorylation of tyrosinase, thereby reducing the activation of tyrosinase.

2. A method of reducing activation of tyrosinase in vertebrate epidermal melanocytes comprising introducing into the melanocytes a tyrosinase phosphorylation site mimic which binds to protein kinase C-beta, thereby reducing protein kinase C-beta binding to tyrosinase and thereby reducing the activation of tyrosinase.

3. A method of reducing activation of tyrosinase in vertebrate epidermal melanocytes, comprising inhibiting protein kinase C-beta-mediated phosphorylation of a serine residue of the tyrosinase cytoplasmic domain wherein the phosphorylation of serine residue 505 is inhibited.

4. A method of reducing activation of tyrosinase in vertebrate epidermal melanocytes, comprising inhibiting the protein kinase C-beta-mediated phosphorylation of a serine residue of the tyrosinase cytoplasmic domain wherein the phosphorylation of serine residue 509 is inhibited.

5. A method of reducing activation of tyrosinase in vertebrate epidermal melanocytes comprising introducing into the melanocytes a peptide that specifically interferes with the protein kinase C-beta-mediated phosphorylation of serine residues in the cytoplasmic domain of tyrosinase.

6. The method of claim 5 wherein the phosphorylation of serine residue 505 is inhibited.

7. The method of claim 5 wherein the phosphorylation of serine residue 509 is inhibited.

8. The method of claim 5 wherein the peptide comprises an amino acid sequence homologous to the amino acid sequence comprising the site of the cytoplasmic domain of tyrosinase where protein kinase C-beta-mediated phosphorylation occurs.

9. The method of claim 8 wherein the peptide comprises from about 5 to about 30 amino acid residues and at least one of the residues is a serine.

10. The method of claim 9 wherein the peptide comprises amino acid sequence SEQ ID NO:1 or SEQ ID NO:4.

11. A method of decreasing pigmentation in vertebrate skin, hair, wool or fur comprising inhibiting the protein kinase C-beta-mediated phosphorylation of a serine residue in the cytoplasmic domain of tyrosinase contained in epidermal melanocytes.

12. The method of claim 11 wherein the phosphorylation of serine residue 505 is inhibited.

13. The method of claim 11 wherein the phosphorylation of serine residue 509 is inhibited.

14. The method of claim 11 wherein a peptide that specifically interferes with the protein kinase C-beta-mediated phosphorylation of a serine residue in the cytoplasmic domain of tyrosinase is introduced into epidermal melanocytes.

15. The method of claim 14 wherein the peptide comprises an amino acid sequence homologous to the amino acid sequence comprising the site of the cytoplasmic domain of tyrosinase where protein kinase C-beta-mediated phosphorylation occurs.

16. The method of claim 15 wherein the peptide comprises from about 5 to about 30 amino acid residues and at least one of the residues is a serine.

17. The method of claim 16 wherein the peptide comprises amino acid sequence SEQ ID NO:1 or SEQ ID NO:4.

18. The method of claim 14 wherein the peptide is introduced into the epidermal melanocytes by topical administration of a pharmaceutical composition containing the peptide.

19. A method of decreasing pigmentation in vertebrate skin, hair, wool or fur comprising inhibiting the phosphorylation of tyrosinase in vertebrate epidermal melanocytes contained in skin or hair, wool or fur bulbs comprising topically applying to the skin or skin surrounding hair, wool or fur bulbs of the vertebrate, a peptide encapsulated into liposomes wherein the peptide comprises an amino acid sequence homologous to the amino acid sequence comprising the site of the cytoplasmic domain of tyrosinase where protein kinase C-beta-mediated phosphorylation occurs, whereby the peptide is introduced into the melanocytes and phosphorylation of tyrosinase is inhibited, thereby decreasing pigmentation.

* * * * *